United States Patent
Rambach

(10) Patent No.: US 9,328,373 B2
(45) Date of Patent: May 3, 2016

(54) DETECTION OF *SALMONELLA* LACTOSE⁺

(76) Inventor: Alain Rambach, Paris (FR)

(*) Notice: Subject to any disclaimer, the term of this patent is extended or adjusted under 35 U.S.C. 154(b) by 1771 days.

(21) Appl. No.: 11/990,976

(22) PCT Filed: Aug. 25, 2006

(86) PCT No.: PCT/EP2006/065684
§ 371 (c)(1),
(2), (4) Date: May 11, 2009

(87) PCT Pub. No.: WO2007/023185
PCT Pub. Date: Mar. 1, 2007

(65) Prior Publication Data
US 2010/0297690 A1    Nov. 25, 2010

(30) Foreign Application Priority Data
Aug. 26, 2005  (FR) .................................... 05 08770

(51) Int. Cl.
C12Q 1/04      (2006.01)
C12N 1/20      (2006.01)

(52) U.S. Cl.
CPC ........ *C12Q 1/045* (2013.01); *C12N 1/20* (2013.01); *G01N 2333/255* (2013.01)

(58) Field of Classification Search
None
See application file for complete search history.

(56) References Cited

U.S. PATENT DOCUMENTS 7,235,379 B2 * 6/2007 Roger-Dalbert ................ 435/34

FOREIGN PATENT DOCUMENTS

| EP | 0 326 635 | 8/1989 |
|----|-----------|--------|
| FR | 2 697 028 | 1/1995 |
| WO | WO-92/17607 | 10/1992 |
| WO | WO-99/41409 | 8/1999 |
| WO | WO-99-50438 | 10/1999 |

OTHER PUBLICATIONS

Perry et al. "Fundamental aspects of enzyme/chromogenic substrate interactions in agar medium formulations for esterase and glycosidase in *Salmonella*". In: *Salmonella* and Salmonellosis 1997 Proceedings, Ploufragan, France, pp. 63-70.*
Caroline Cox. "Nonyl phenol and related chemicals". Journal of Pesticide Reform. 1996, vol. 16, No. 1, pp. 15-20.*
The Dow Chemical Company Material Safety Sheet Tergitol NP-9 Surfactant dated Feb. 24, 2003, pp. 1-17.*
The Dow Chemical Company Material Safety Sheets Tergitol NP-4 Surfactant dated Feb. 10, 2003, pp. 1-17.*
International Search Report and Written Opinion from International Application No. PCT/EP2006/065684 dated Oct. 23, 2006.
Tergitol-8,Niaproof-8 [online] [retrieved Sep. 21, 2011]. Retrieved from the Internet: <URL: http://www.chem-info.com/product/Tergitol-8-104799.html> 1 page.
Sodium Tetradecyl Sulfate [PharmGKB] [online] [retrieved Sep. 21, 2011]. Retrieved from the Internet: <URL: http://www.pharmgkb.org/do/serve?objId=PA164746759&objCls=Drug> 1 page.
Nonylphenol—Wikipedia, the free encyclopedia [online] Retrieved from the Internet Jul. 17, 2012 <URL: http://en.wikipedia.org/wiki/Nonylphenol>; 3 pages.
Tergitol™ NP-Series Surfactants; Dow; Jun. 23, 2004; 1 page.
Tergitol™ NP-9 Surfactant; Dow; Technical Data Sheet [online] [retrieved from the Internet Aug. 5, 2015] <URL: http://www.dow.com/scripts/litorder.asp?filepath=surfactants/pdfs/noreg/119-01919.pdf> 2 pages.
DOW Surfactants; A Guide to Products and Performance for Household and Institutional & Industrial Cleaners; DOW; dated Jan. 2002; 12 pages.
TRITON XL-80N Suppliers Manufactures [online] [retrieved from the Internet Jul. 17, 2012] <URL: http://www.guidechem.com/products/68603-25-8.html> 2 pages.
Popper, Zoe A., et al.; "*Plant and Algal Cell Walls: Diversity and Functionality*"; Annals of Botany; 114: pp. 1043-1048; 2014.

* cited by examiner

*Primary Examiner* — Vera Afremova
(74) *Attorney, Agent, or Firm* — Alston & Bird LLP

(57) ABSTRACT

The invention relates to a medium for the detection and/or identification of *Salmonella*, including *Salmonella* lactose⁺.

14 Claims, No Drawings

DETECTION OF SALMONELLA LACTOSE+

The present patent application is a non-provisional of International Application No. PCT/EP2006/065684, filed Aug. 25, 2006.

This invention relates to a medium for the detection and/or identification of Salmonellas.

The detection and identification of *Salmonella* bacteria, pathogenic for humans, is a major problem in medical bacteriology and in monitoring food-industry hygiene.

In particular, this bacterium is responsible for typhoid fever and food poisoning in humans.

In cases of epidemics caused by poultry farming, birds with gastrointestinal tract infections are not actually ill but act as *Salmonella* reservoirs. These bacteria can then be transmitted in food, especially by eggs. *Salmonella* is also a bacterium that requires compulsory notification.

It is therefore necessary to set up large-scale systems for the detection of infected sites and, more particularly, infected farms in order to reduce the scale of such epidemics and limit contamination.

Detection of Salmonellas is usually carried out on a gelose selective isolation medium for enterobacteria allowing differentiation of pathogenic enterobacteria and detection of suspect *Salmonella* colonies. An ideal detection and/or identification medium must allow growth of enterobacteria and the differentiation of various species present in order to make it possible to carry out later identification of one colony of each type and to allow for detection of suspect *Salmonella* colonies.

More particularly, it is important to detect Salmonellas, which are lactose$^-$ on the whole. However, it is also important to be able to detect lactose$^+$ *Salmonella* strains which, while representing only a low percentage of total *Salmonella* strains encountered, notably in the food industry, are often identified as *Escherichia coli* and therefore give rise to false positive results.

It has, in fact, quite mistakenly been believed for many years that fermentation in the presence of lactose makes it possible to distinguish between *Salmonella* bacteria and other Enterobacteriaceae. It has been known for a very long time that *Escherichia coli* is lactose$^+$ whereas *Salmonella* is lactose$^-$. Discovery of lactose$^+$ *Salmonella* strains therefore revealed the lack of reliability of tests based on the lactose properties of enterobacteria and brings out the importance of detection of lactose$^+$ *Salmonella*.

The object of this invention is to make it possibly to perform routine tests for the detection and identification of Salmonellas, for example using monitoring methods for the microbiological quality of water using soaking methods, or monitoring the microbiological quality of food-production factories by means of contact methods, diagnosis or even tests for pathogenic microorganisms by means of conventional microbiological tests with Petri dishes on solid or semi-solid media, with the aid of media in accordance with the invention.

The object of this invention is to increase the sensitivity and selectivity of the detection and differentiation of Salmonellas in a contaminated sample by means of a culture medium which, while allowing detection of the esterase activity particular to these bacteria, enables increased differentiation of Salmonellas among other enterobacteria, including lactose$^+$ *Salmonella*.

The person skilled in the art is already aware of culture media intended for the detection of Salmonellas using chromogenic agents (patent FR 2 197 028, Rambach) but while this type of medium might make it possible to distinguish between Salmonellas and other enterobacteria, it does not necessarily make it possible to characterize lactose$^+$ Salmonellas.

The media of the prior art have also generally been based on the lactose$^-$ or beta-galactosidase$^-$ properties of Salmonellas.

The medium of the invention for detection and/or identification of Salmonellas comprises a chromogen bound to caprylate or one of its derivatives, an esterase substrate, which is released into the medium under the effect of these enzymes and thus resulting in the identification of *Salmonella* colonies.

Nevertheless, in order to increase the selectivity and sensitivity of the medium of the invention to allow detection of lactose$^+$ Salmonellas, said medium also includes a detergent from the nonylphenol ethoxylate family.

Unexpectedly, it has been found that the addition of such a detergent to the medium of the invention at a suitable concentration compatible with good *Salmonella* growth results in not only easier detection of *Salmonella* but also detection of lactose$^+$ *Salmonella*.

Among the nonylphenol ethoxylates that can be used within the scope of this invention, the following can be cited in particular: Tergitol® NP (sold by The Dow Chemical Company) and in particular Tergitol® NP-7 and Tergitol® NP-9, also called Igepal® CO-630 or Triton® N-60. This is α-(nonylphenyl)-ω-hydroxypoly(oxy-1,2-ethanediyl).

Preferentially, the suitable detergent will be used at a concentration of 0.5 and 2.5 g/l, preferably from 1 to 2 g/l and or preferentially still from 1.3 to 1.7 g/l.

According to a preferred embodiment of the invention, the chromogenic compound is a caprylic acid ester, advantageously chosen from the group comprising the indolyl caprylate derivatives and hydroxy-quinoline caprylate derivatives as well as their salts. Among these derivates, the following an be cited in particular: halogeno-indolyl caprylate derivatives (bromo-indolyl caprylate, chloro-indolyl caprylate, fluoro-indolyl caprylate, iodo-indolyl caprylate, dichloro-indolyl caprylate, chloro-bromo-indolyl caprylate, tri-chloro-indolyl caprylate) and methyl-indoxyl-caprylate derivatives.

More particularly still, the caprylic acid ester is chosen from the group comprising the derivatives of 6-chloro-indolyl-caprylate, 5-bromo-indolyl-caprylate, 3-bromo-indolyl-caprylate, 6-fluoro-indolyl-caprylate, 5-iodo-indolyl-caprylate, 4,6-dichloro-indolyl-caprylate, 6,7-dichloro-indolyl-caprylate, 5-bromo-4-chloro-indolyl-caprylate, 5-bromo-6-chloro-indolyl-caprylate, 4,6,7-trichloro-indolyl-caprylate, N-methyl-indolyl-caprylate and 8-hydroxy-quinoline caprylate.

Preferentially, the suitable detergent will be used art a concentration between 0.1 and 0.4 g/l, preferably between 0.15 and 0.3 g/l.

The person skilled in the art is perfectly well-equipped to complete the medium of the invention with the aim of eliminating bacterial other than Salmonellas, for example by testing other bacteria for characteristics not found in Salmonellas which is, in particular, beta-galactosidase$^-$. Consequently, the medium of the invention can also contain derivatives of beta-glucoside linked to a chromaphore that is different from the one used to detect Salmonellas.

The medium of the invention therefore makes it possible to detect and identify a stained *Salmonella* colony more obviously, even in the presence of thousands of other colonies on a solid or semi-solid medium. In fact, the *Salmonella* colonies detected by the medium of the invention are stained with a particular colour while other microorganisms are stained a different colour or have no colour at all.

Detection of *Salmonella* colonies within the scope of this invention is direct in the sense that it requires no other action or intervention after fermentation of colonies, such as the use of any type of dye or particular light.

This invention also relates to a method for the detection and/or identification of Salmonellas in any sample including inoculation of the culture medium of the invention with the sample to be tested and detection of the colour indicative of the presence of *Salmonella* colonies.

Depending on the form and presentation of the medium and as a function of the type of protection carried out, inoculation is preferably performed by contact, soaking, on the surface or within the body of it.

The example below is given solely for the purpose of illustrating the invention and can in no way considered to be limiting.

EXAMPLE

Detection of Salmonellas

I. According to a first series of experiments, several media were tested for detection and differentiation of *E. coli* (the main constituent of the commensal flora of samples in which the presence of Salmonellas are investigated) and *Salmonella* (in particular lactose⁺ *Salmonella*).

Each of the said media consists of the base to which other compounds are added as listed below:
Base (g/l)
Meat or yeast extract 3
Peptone 5
Sodium chloride 5
Agar 15
5-bromo-6-chloro-3-indolyl caprylate 0.2
5-bromo-4-chloro-3-indolyl beta glucoside 0.1
    Medium A (g/l)
Base
+Sodium deoxycholate 2.5
    Medium B (g/l)
Base
+Sodium deoxycholate 1.5
+Triton XL-80N deoxycholate 1.5
    Medium C of the invention (g/l)
Base
+Sodium deoxycholate 1.5
+Tergitol NP-9 deoxycholate 1.5

|  | Medium | | |
|---|---|---|---|
|  | A | B | C |
| *Salmonella* spp | + | + | ++ |
| Lactose positive *Salmonella* | + | + | ++ |
| *E. coli* | + | + | Colourless |

"+" represents the intensity of the mauve colour obtained

Only the medium of the invention (C) makes it possible to distinguish *Salmonella* spp and lactose⁺ *Salmonella* from *E. coli*.

II. Another series of experiments consisted in comparing the above-described medium C of the invention with XLT4 medium (Xylose-Lysine-Teritol (Niaproof) 4) for detection of *Salmonella* including lactose⁺ strains.

|  | Medium | |
|---|---|---|
|  | XLT4 | C |
| *Salmonella* spp (ATCC 35640) | + | + |
| lactose⁺ *Salmonella* senftenberg (321) | − | + |

Only the medium of the invention (C) made it possible to detect all strains of *Salmonella*.

The invention claimed is:

1. A medium for the detection of *Salmonella* comprising a chromogenic substrate of caprylate esterase or one of its salts and a detergent from the nonylphenol ethoxylate family.

2. The medium according to claim 1, wherein the chromogenic substrate of caprylate esterase is an ester of caprylic acid.

3. The medium according to claim 2, wherein the caprylic acid ester is chosen from the group consisting of indolyl caprylate derivatives and hydroxy-quinoline caprylate derivatives.

4. The medium according to claim 3, wherein the caprylic acid ester is chosen from the group comprising the derivatives of halogeno-indolyl caprylate derivatives and methyl-indoxyl-caprylate derivatives.

5. The medium according to claim 3, wherein the caprylic acid ester is chosen from the group comprising the derivatives of 6-chloro-indolyl-caprylate, 5-bromo-indolyl-caprylate, 3-bromo-indolyl-caprylate, 6-fluoro-indolyl-caprylate, 5-iodo-indolyl-caprylate, 4,6-dichloro-indolyl-caprylate, 6,7-dichloro-indolyl-caprylate, 5-bromo-4-chloro-indolyl-caprylate, 5-bromo-6-chloro-indolyl-caprylate, 4,6,7-trichloro-indolyl-caprylate, N-methyl-indolyl-caprylate and 8-hydroxy-quinoline caprylate.

6. The medium according to claim 5, wherein the derivative is 5-bromo-6-chloro-3-indolyl caprylate.

7. The medium according to claim 1, wherein the detergent is chosen from the group comprising TERGITOL® NP-9, IGEPAL® CO-630 and TRITON® N-60.

8. The medium according to claim 7, wherein TERGITOL® NP-9 is present in the said medium at a concentration of 0.5 to 2.5 g/l.

9. A method for the detection of *Salmonella* comprising the following steps: inoculating a medium according to one of claims 1 to 8 with a sample suspected of comprising *Salmonella*, and detecting a change in color in the sample that is indicative of the presence of *Salmonella* in the sample.

10. The medium according to claim 4, wherein the halogeno-indolyl caprylate derivative is chosen from the group consisting of: bromo-indolyl caprylate, chloro-indolyl caprylate, fluoro-indolyl caprylate, iodo-indolyl caprylate, dichloro-indolyl caprylate, chloro-bromo-indolyl caprylate, tri-chloro-indolyl caprylate.

11. The medium according to claim 8, wherein TERGITOL® NP-9 is present at a concentration of 1 to 1.7 g/l.

12. The medium according to claim 8, wherein TERGITOL® NP-9 is present at a concentration of 1.3 to 1.7 g/l.

13. The medium according to claim 1, further comprising 5-bromo-4-chloro-3-indolyl beta glucoside.

14. The medium according to claim 1, wherein the medium differentiates between lactose+ *Salmonella* and *Escherichia coli*.

\* \* \* \* \*